(12) United States Patent
Derrien et al.

(10) Patent No.: US 10,960,033 B2
(45) Date of Patent: Mar. 30, 2021

(54) **COMPOSITIONS AND METHODS FOR INCREASING OR MAINTAINING *FAECALIBACTERIUM PRAUSNITZII* POPULATIONS**

(71) Applicant: COMPAGNIE GERVAIS DANONE, Paris (FR)

(72) Inventors: Muriel Derrien, Bures-sur-Yvette (FR); Mathilde Lebas, Petit-Couronne (FR); Peggy Garault, Montlhéry (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 101 days.

(21) Appl. No.: 16/064,356

(22) PCT Filed: Dec. 23, 2015

(86) PCT No.: PCT/EP2015/081148
§ 371 (c)(1),
(2) Date: Jun. 20, 2018

(87) PCT Pub. No.: WO2017/108126
PCT Pub. Date: Jun. 29, 2017

(65) Prior Publication Data
US 2019/0000893 A1    Jan. 3, 2019

(51) Int. Cl.
*A61K 35/744* (2015.01)
*C12R 1/46* (2006.01)
*A23L 33/135* (2016.01)
*A23C 9/123* (2006.01)
*C12N 1/20* (2006.01)

(52) U.S. Cl.
CPC ............ *A61K 35/744* (2013.01); *A23C 9/123* (2013.01); *A23C 9/1236* (2013.01); *A23C 9/1238* (2013.01); *A23L 33/135* (2016.08); *C12N 1/20* (2013.01); *C12R 1/46* (2013.01); *A23V 2002/00* (2013.01); *A23Y 2240/41* (2013.01); *A23Y 2240/75* (2013.01)

(58) Field of Classification Search
CPC .................................................... A23C 9/1238
See application file for complete search history.

(56) References Cited

FOREIGN PATENT DOCUMENTS

| WO | WO 2013/130624 A2 | 9/2013 |
|---|---|---|
| WO | WO 2014/137211 A1 | 9/2014 |

OTHER PUBLICATIONS

Gullón et al., "Assessment of prebiotic potential of Akpan-yoghurt-like product and effects on the human intestinal microbiota," Jour. of Functional Foods, vol. 19, 2015, pp. 545-553.
International Search Report issued in International Patent Application No. PCT/EP2015/081148, dated Feb. 17, 2016 (4 pages).
Martín et al., "Role of commensal and probiotic bacteria in human health: a focus in inflammatory bowel disease," Microbial Cell Factories, vol. 12, 2013, pp. 1-11.
Miquel et al., "Faecalibacterium prausnitzii and human intestinal health," Current Opinion in Microbiology, vol. 16(3), 2013, pp. 255-261.
Purwandari et al., "Effects of exopolysaccharide-producing strains of *Streptococcus thermophilus* on technological and rheological properties of set-type yoghurt," International Dairy Journal, vol. 17, 2007, pp. 1344-1352.
Thomas et al., "Probiotics: a proactive approach to health. A symposium report," British Journal of Nutrition, vol. 114, 2015, pp. S1-S15.
Van Hylckama Vlieg et al., "Impact of microbial transformation of food on health—from fermented foods to fermentation in the gastro-intestinal tract," Current Opinion in Biotechnology, vol. 22, 2011, pp. 211-219.

*Primary Examiner* — Bin Shen
(74) *Attorney, Agent, or Firm* — Arent Fox LLP

(57) ABSTRACT

The present invention relates to the use of at least one lactic acid bacterium, or a composition comprising thereof or conditioned thereby, for increasing or maintaining a *Faecalibacterium prausnitzii* population.

17 Claims, 1 Drawing Sheet

COMPOSITIONS AND METHODS FOR INCREASING OR MAINTAINING *FAECALIBACTERIUM PRAUSNITZII* POPULATIONS

CROSS REFERENCE TO RELATED APPLICATIONS

This application is a 35 U.S.C. 371 National Phase of PCT Application No. PCT/EP2015/081148 filed Dec. 23, 2015.

FIELD OF THE INVENTION

The present invention relates to compositions and methods for increasing or maintaining *Faecalibacterium prausnitzii* populations.

TECHNICAL BACKGROUND

*Faecalibacterium prausnitzii* (*F. prausnitzii*) is the most abundant bacterium in the human intestine of healthy adults, representing more than 5% of the total bacterial population. Over the past years, an increasing number of studies have described the importance of this metabolically active commensal bacterium as a component of the healthy human microbiota. The major end products of glucose fermentation by *F. prausnitzii* strains are formate, small amounts of D-lactate and substantial quantities of butyrate. Indeed, *F. prausnitzii* is one of the most abundant butyrate-producing bacterium in the gastro-intestinal tract. Butyrate plays a major role in gut physiology and it has pleiotropic effects in intestinal cell life cycle. Changes in the abundance of *F. prausnitzii* have been linked to dysbiosis in several human disorders.

In this regard, International publication WO 2014/070014 reports that oral administration of riboflavin, i.e. vitamin B2, is capable of increasing the absolute and relative concentration of *F. prausnitzii*, as well as enhancing butyrate production, in human volunteers.

However, vitamin B2 is notably sensitive to light, heat and oxygen, which limits the food-production processes in which it can be used. In addition, not all food products can be supplemented by a vitamin.

Accordingly, there is still a need for alternatives to riboflavin for increasing or maintaining *F. prausnitzii* populations.

SUMMARY OF THE INVENTION

The present invention follows from the unexpected finding that a culture of *Streptococcus thermophilus* or *Lactococcus lactis* subsp. *lactis* can be used to increase the growth of *Faecalibacterium prausnitzii* or the production of butyrate by this bacterium.

Accordingly, the present invention relates to the use, in particular the non-therapeutic use, of at least one lactic acid bacterium, or a composition comprising thereof or conditioned thereby, for increasing or maintaining a *Faecalibacterium prausnitzii* population, in particular a *Faecalibacterium prausnitzii* intestinal population in an individual, and/or for increasing or maintaining butyrate production, in particular intestinal butyrate production, in an individual.

The present invention also relates to a method, in particular a non-therapeutic method, for increasing or maintaining a *Faecalibacterium prausnitzii* intestinal population in an individual and/or for increasing or maintaining intestine production in an individual, comprising feeding, providing or administering, the individual a composition as defined above, in particular in an effective amount.

The present invention also relates to a composition comprising, or conditioned by, at least one lactic acid bacterium for use in a method for increasing or maintaining a *Faecalibacterium prausnitzii* population, in particular a *Faecalibacterium prausnitzii* intestinal population in an individual, and/or for increasing or maintaining butyrate production, in particular intestinal butyrate production in an individual.

The present invention also relates to the use of at least one lactic acid bacterium, or a composition comprising thereof or conditioned thereby, for the manufacture of a food product intended for increasing or maintaining a *Faecalibacterium prausnitzii* population, in particular a *Faecalibacterium prausnitzii* intestinal population in an individual, and/or for increasing or maintaining butyrate production, in particular intestinal butyrate production in an individual.

The present invention also relates to a *Streptococcus thermophilus* strain deposited at the CNCM under reference number CNCM I-3862.

The present invention also relates to a fermented dairy product comprising a *Streptococcus thermophilus* strain deposited at the CNCM under reference number CNCM I-3862.

DETAILED DESCRIPTION OF THE INVENTION

As intended herein "at least one lactic acid bacterium or a composition comprising thereof" shall be taken to mean a composition comprising at least one lactic acid bacterium.

As intended herein a composition "conditioned thereby" means that that the composition comprises secretions from lactic acid bacteria according to the invention. By way of example, the composition conditioned by lactic acid bacteria according to the invention may comprise the supernatant of a culture of lactic acid bacteria or it can be a dairy product fermented by lactic acid bacteria from which the lactic acid bacteria have been removed.

As used herein the term "supernatant" shall be taken to mean the culture medium in which bacteria has been grown under conditions suitable for growth. The culture media may be separated from the bacterial cells and fragments thereof by means of centrifugation.

As used herein the term "stable composition" shall be taken to mean a composition that does not present sedimentation and/or serum separation.

As used herein the term "x % (w/w)" is equivalent to "x g per 100 g".

As used herein the term "fermented milk" shall be taken to mean a product or composition derived from milk by the acidifying action of at least one lactic acid bacterium.

As used herein the term "spoonable" shall be taken to mean a solid or semi-solid that may be consumed by means of a spoon or other utensil.

As used herein the term "fermentation" shall be taken to mean the metabolism of a substance by bacteria, yeasts, or other microorganisms.

As used herein the term "cfu" or "CFU" shall be taken to be an abbreviation of the term "colony forming unit".

As used herein the term "CNCM I-" followed by a 4 digit number shall be taken to refer to a strain deposited at the Collection Nationale de Cultures de Microorganismes (CNCM) 25 rue du Docteur Roux, Paris, France under the Budapest Treaty with an accession number corresponding to said 4 digit number, e.g. CNCM I-3862.

As used herein reference to a bacterial strain or species shall be taken to include functionally equivalent bacteria derived therefrom such as but not limited to mutants, variants or genetically transformed bacteria. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or prophylactic interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling". In the present text, strains, mutants and variants derived from a parent species or strain will be considered as being encompassed by reference to said parent species or strain, e.g. the phrases "*S. thermophilus*" and "strain CNCM I-3862" shall be taken to include strains, mutants and variants derived therefrom.

Accordingly, as used herein reference to a bacterial strain specified by an accession or deposit number shall be taken to encompass variants thereof having at least 80% identity with the 16S rRNA sequence of said specified strain, preferably at least 85% identity, more preferably at least 90% identity, further preferably at least 95% identity (see: Stackebrandt & Goebel, 1994, Int. J. Syst. Bacteriol. 44:846-849). In a particularly preferred embodiment, said variant has at least 97% identity with the 16S rRNA sequence of said specified strain, more preferably at least 98% identity, more preferably at least 99% identity.

The lactic acid bacteria comprised in the composition according to the invention may be living or dead bacteria. Preferably, at least some of the lactic acid bacteria comprised in the composition according to the invention are living bacteria. More preferably, the composition according to the invention comprises from $10^5$ to $10^{10}$ colony forming unit of lactic acid bacteria per gram of composition (CFU/g), more preferably at least $10^7$, $10^8$, $10^9$ colony forming unit of lactic acid bacteria per gram of composition (CFU/g).

The composition according to the invention is preferably a food or nutritional composition, i.e. a food product, more preferably a dairy product, and most preferably a fermented dairy product, in particular fermented by the lactic acid bacteria according to the invention.

As intended herein a fermented dairy product is the fermentation product of a milk-based composition by a starter culture of fermenting microorganisms, in particular bacteria, more particularly lactic acid bacteria. The fermented dairy product according to the invention can thus be a fermented milk, a yoghurt, in particular a set, stirred or drink yogurt, or a fresh cheese such as a white cheese or a petit-Suisse. It can be also a strained fermented dairy product such as a strained yoghurt also called concentrated yoghurt or Greek-style yoghurt.

The terms "fermented milk" and "yogurt" or "yoghurt" are given their usual meanings in the field of the dairy industry, that is, products destined for human consumption and originating from acidifying lactic fermentation of a milk substrate. These products can contain secondary ingredients such as fruits, vegetables, sugar, etc.

The expression "fermented milk" is thus reserved in the present application for a dairy product prepared with a milk substrate which has undergone treatment at least equivalent to pasteurization, seeded with microorganisms belonging to the characteristic species or species of each product.

The term "yogurt" or "yoghurt" is reserved for fermented milk obtained, according to local and constant usage, by the development of specific thermophilic lactic bacteria known as *Lactobacillus delbrueckii* subsp. *bulgaricus* and *Streptococcus thermophilus*, which must be in the living state in the finished product, at a minimum rate. In certain countries, regulations require the addition of other lactic bacteria to the production of yoghurt, and especially the additional use of strains of *Bifidobacterium* and/or *Lactobacillus acidophilus* and/or *Lactobacillus casei*. These additional lactic strains are intended to impart various properties to the finished product, such as that of favouring equilibrium of intestinal flora or modulating the immune system.

In practice, the expression "fermented milk" is therefore generally used to designate fermented milks other than yogurts. It can also, according to country, be known by names as diverse as, for example, "Kefir", "Kumtss", "Lassi", "Dahi", "Leben", "Filmjolk", "Villi", "*Acidophilus* milk".

Finally, the name "white cheese" or "petit-Suisse" is, in the present application, reserved for unrefined non-salty cheese, which has undergone fermentation by lactic acid bacteria only (and no fermentation other than lactic fermentation).

The fermented dairy product can be made from whole milk and/or wholly or partly skimmed milk, which can be used in a powder form which can be reconstituted by addition of water. Other milk components can be added such as cream, casein, caseinate (for example calcium or sodium caseinate), whey proteins notably in the form of a concentrate (WPC), milk proteins notably in the form of a concentrate (MPC), milk protein hydrolysates, and mixtures thereof. The milk and milk components has typically an animal origin such as a cow, goat, sheep, buffalo, donkey or camel origin.

As intended herein, a "lactic acid bacterium" is a Gram-positive, acid-tolerant, generally non-sporulating and non-respiring, either rod- or cocci-shaped bacterium that is able to ferment sugars in lactic acid.

Preferably, the at least one lactic acid bacterium according to the invention belongs to a genus selected from the group consisting of the *Lactobacillus, Lactococcus, Streptococcus* and *Bifidobacterium* genera, most preferably the at least one lactic acid bacterium according to the invention is of the genus *Streptococcus* or *Lactococcus*.

Preferably the at least one lactic acid bacterium according to the invention is *Streptococcus thermophilus* or *Lactococcus lactis*, in particular *Lactococcus lactis* subsp. *lactis*.

Preferably the lactic acid bacterium is *Streptococcus thermophilus* CNCM I-3862

The strain *Streptococcus thermophilus* CNCM I-3862 has been deposited at the Collection Nationale de Cultures de Microorganismes (CNCM) (Institut Pasteur, 25 Rue du Docteur Roux, Paris, France) under the Budapest Treaty on Oct. 31, 2007 under reference number CNCM I-3862.

Preferably the lactic acid bacterium is *Lactococcus lactis* subsp. *lactis* CNCM I-1631. The strain *Lactococcus lactis* subsp. *lactis* CNCM I-1631 has been deposited at the Collection Nationale de Cultures de Microorganismes (CNCM) (Institut Pasteur, 25 Rue du Docteur Roux, Paris, France) under the Budapest Treaty on Oct. 24, 1995 under reference number CNCM I-1631.

As intended herein "increasing or maintaining" a *Faecalibacterium prausnitzii* population, in particular an intestinal population thereof, means protecting, favoring or stimulating the growth of *Faecalibacterium prausnitzii* bacteria so that the count of *Faecalibacterium prausnitzii* bacteria, or the relative number of *Faecalibacterium prausnitzii* bacteria with respect to other bacteria, is maintained or increases.

As intended herein an intestinal population of *Faecalibacterium prausnitzii* relates to the *Faecalibacterium prausnitzii* bacteria present in the intestine or gut, in particular the colon, of an individual.

Determining the quantity of *Faecalibacterium prausnitzii* bacteria in a sample can be performed by numerous methods well known to one of skill in the art. Determining the intestinal quantity of *Faecalibacterium prausnitzii* bacteria in an individual can be performed by culturing stool samples of the individual.

As intended herein butyrate includes both its acid and base forms, i.e. butryric acid and butyrate sensu stricto. Butryrate is also named butanoate and has the formula $CH_3CH_2CH_2-COO^-$.

As intended herein "increasing or maintaining" butyrate production, in particular the intestinal production thereof, means protecting, favoring or stimulating the production of butyrate so that it is maintained or increases. Preferably, within the frame of the present invention, butyrate is produced by *Faecalibacterium prausnitzii* bacteria, in particular in an individual's intestine.

Preferably, the individual according to the invention is a human individual. In one embodiment, the individual according to the invention is a healthy individual or an individual who does not suffer from intestinal diseases or diseases of the gastrointestinal tact As intended herein "non-therapeutic" means that the individual receiving or consuming the composition according to the invention is not treated for a disease by the composition. In other words, within the frame of the non-therapeutic uses and methods according to the invention, the composition according to the invention is neither a medicament nor a pharmaceutical composition.

Uses & Methods

In one aspect the present invention provides the use of at least one lactic acid bacterium, or a composition comprising thereof or conditioned thereby, for increasing or maintaining a *Faecalibacterium prausnitzii* population. Typically the *Faecalibacterium prausnitzii* population is the intestinal population in an individual.

In a further aspect the present invention provides the use of at least one lactic acid bacterium, or a composition comprising thereof or conditioned thereby, for increasing or maintaining butyrate production in an individual. Typically the butyrate production is the intestinal butyrate production in an individual.

In an alternative embodiment the present invention also provides a method for increasing or maintaining a *Faecalibacterium prausnitzii* population comprising feeding, providing or administering to the individual a composition as defined above, in particular in an effective amount thereof. Typically the *Faecalibacterium prausnitzii* population is the intestinal population in an individual.

In a further alternative embodiment the present invention also provides a method for increasing or maintaining butyrate production in an individual comprising feeding, providing or administering, to the individual a composition as defined above, in particular in an effective amount thereof. Typically the butyrate production is the intestinal butyrate production in an individual. Determination of an effective amount can be carried out by the skilled person, particularly in view of the disclosure provided herein.

Preferably, the at least one lactic acid bacterium according to the invention belongs to a genus selected from the group consisting of the *Lactobacillus, Lactococcus, Streptococcus* and *Bifidobacterium* genera, most preferably the at least one lactic acid bacterium according to the invention is of the genus *Streptococcus* or *Lactococcus*.

Preferably the at least one lactic acid bacterium according to the invention is *Streptococcus thermophilus* or *Lactococcus lactis*, in particular *Lactococcus lactis* subsp. *lactis*.

Preferably the lactic acid bacterium is *Streptococcus thermophilus* CNCM I-3862. The strain *Streptococcus thermophilus* CNCM I-3862 has been deposited at the Collection Nationale de Cultures de Microorganismes (CNCM) (Institut Pasteur, 25 Rue du Docteur Roux, Paris, France) under the Budapest Treaty on Oct. 31, 2007 under reference number CNCM I-3862.

Preferably the lactic acid bacterium is *Lactococcus lactis* subsp. *lactis* CNCM I-1631. The strain *Lactococcus lactis* subsp. *lactis* CNCM I-1631 has been deposited at the Collection Nationale de Cultures de Microorganismes (CNCM) (Institut Pasteur, 25 Rue du Docteur Roux, Paris, France) under the Budapest Treaty on Oct. 24, 1995 under reference number CNCM I-1631.

It is particularly preferred that the uses and methods as described herein are non-therapeutic uses and methods.

Compositions & Strains

The present invention also relates to a composition comprising, or conditioned by, at least one lactic acid bacterium for use in increasing or maintaining a *Faecalibacterium prausnitzii* population, in particular a *Faecalibacterium prausnitzii* intestinal population in an individual, and/or for increasing or maintaining butyrate production, in particular intestinal butyrate production in an individual.

The composition for use according to embodiments of the invention is suitable for consumption or ingestion, preferably by oral means. Accordingly the composition comprises or consists of comestible matter. It is particularly preferred that the compositions of embodiments of the invention are substantially free of pathogenic or toxicogenic matter. The composition according to embodiments of the invention may be a medicament or pharmaceutical composition. In a particularly preferred embodiment the composition according to the invention may be a non-therapeutic composition, preferably a nutraceutical composition, a nutritional composition and/or a food composition.

The present invention also relates to the intended use of at least one lactic acid bacterium as provided herein for the manufacture of a food composition for increasing or maintaining a *Faecalibacterium prausnitzii* population, in particular a *Faecalibacterium prausnitzii* intestinal population in an individual, and/or for increasing or maintaining butyrate production, in particular intestinal butyrate production in an individual. It is particularly preferred that the food composition is a fermented food composition, preferably a fermented milk composition. Further compositions according to embodiments of the invention also include baby foods, infant milk formulas and infant follow-on formulas.

Preferably, the composition comprises at least $10^6$, more preferably at least $10^7$ and most preferably at least $10^8$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. Preferably also the composition according to embodiments of the invention comprises at least about $10^7$, more preferably at least $10^{10}$ and most preferably at least $10^9$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In a further embodiment the lactic acid bacteria is selected from the group consisting of CNCM I-1631 & CNCM I-3862.

In embodiments, the composition comprises $10^6$ to $10^{11}$ colony forming unit (CFU) lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^7$ to 1011 colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^8$ to $10^{11}$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^9$ to $10^{11}$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^{10}$ to $10^{11}$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention.

In embodiments, the composition comprises $10^6$ to $10^{10}$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^6$ to $10^9$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^6$ to $10^8$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. In embodiments, the composition comprises $10^6$ to $10^7$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention. It is particularly preferred that the lactic acid bacteria is selected from the group consisting of CNCM I-1631 & CNCM I-3862.

Preferably the composition suitable for the uses and methods of embodiments of the invention comprises milk, more preferably fermented milk. Preferably the composition comprises at least about 30% (w/w) milk, more preferably at least about 50% (w/w) milk and even more preferably at least about 70% (w/w) milk. In embodiments, the composition comprises at 30% to 100% (w/w) milk. In embodiments, the composition comprises 50% to 100% (w/w) milk. In embodiments, the composition comprises 70% to 100% (w/w) milk. Preferably said milk is vegetal and/or animal milk, more preferably soya, almond, oat, hemp, spelt, coconut, rice, goat, ewe, camel, mare or cow milk, and most preferably to cow milk. Preferably said milk(s) are heat-treated, typically pasteurized, to ensure sterility. Preferably said heat treatment is carried out prior to the preparation of the fermented milk composition.

Preferably said milk comprises one or more of skimmed, partially-skimmed or non-skimmed milk. Preferably said milk or milks may be in liquid, powdered and/or concentrated form. In one embodiment said milk further comprises milk components preferably selected from the group consisting of cream, casein, caseinate (for example calcium or sodium caseinate), whey proteins notably in the form of a concentrate (WPC), milk proteins notably in the form of a concentrate (MPC), milk protein hydrolysates, and mixtures thereof. In one embodiment said mixture further comprises plant and/or fruit juices. In one embodiment said milk or milks may be enriched or fortified with further milk components or other nutrients such as but not limited to vitamins, minerals, trace elements or other micronutrients.

Preferably the composition comprises above about 0.3 g per 100 g by weight free lactic acid, more preferably above about 0.7 g or 0.6 g per 100 g by weight free lactic acid. In embodiments, the composition comprises 0.3 g to 0.7 grams per 100 g by weight free lactic acid.

Preferably the composition comprises a protein content at least equivalent to that of the milk or milks from which it is derived, preferably at least about 2.5%, more preferably at least about 3% or 3.5% (w/w). Preferably the composition has a pH equal to or lower than 5, preferably between about 3 and about 4.5 and more preferably between about 3.5 and about 4.5.

Preferably the composition has a viscosity lower than 200 mPa·s, more preferably lower than 100 mPa·s and most preferably lower that 60 mPa·s, at 10° C., at a shear rate of 64 s$^{-1}$. In embodiments, the composition has a viscosity range of 1 to 200 mPa·s, 1 to 100 mPa·s, or 1 to 60 mPa·s, at 10° C., at a shear rate of 64 s$^{-1}$. In embodiments, the composition has a viscosity range of 10 to 200 mPa·s, 10 to 100 mPa·s, or 10 to 60 mPa·s, at 10° C., at a shear rate of 64 s$^{-1}$. In embodiments, the composition has a viscosity range of 30 to 200 mPa·s, 30 to 100 mPa·s, or 30 to 60 mPa·s, at 10° C., at a shear rate of 64 s$^{-1}$.

The composition according to embodiments of the invention is preferably a product selected from the group comprising yogurt, set yogurt, stirred yogurt, pourable yogurt, yogurt drink, frozen yogurt, kefir, buttermilk, quark, sour cream, fresh cheese and cheese. In one embodiment the composition according to embodiments of the invention is a drinkable composition, more preferably a fermented milk drink such as but not limited to a yogurt drink, kefir etc. In an alternative embodiment the composition according to embodiments of the invention is a composition that is spoonable such as a set or stirred yogurt or equivalent thereof.

Preferably the composition, according to embodiments of the invention, may be stored, transported and/or distributed at a temperature of from 1° C. to 10° C. for at least about 30 days, at least about 60 days or at least about 90 days from packaging and remain suitable for consumption.

Preferably, the composition is a packaged product that comprises at least $10^e$, more preferably at least $10^7$ and most preferably at least $10^8$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention subsequent to storage, transport and/or distribution at a temperature of from 1° C. to 10° C. for at least about 30 days, at least about 60 days or at least about 90 days from packaging. It is particularly preferred that the lactic acid bacteria is selected from the group consisting of CNCM I-1631 & CNCM I-3862.

In embodiments, the composition is a packaged product that comprises $10^6$ to $10^8$ or $10^6$ to $10^7$ colony forming unit (CFU) of lactic acid bacteria, preferably *Streptococcus thermophilus* or *Lactococcus lactis* (preferably subsp. *lactis*), according to embodiments of the invention per gram (g) of composition according to embodiments of the invention subsequent to storage, transport and/or distribution at a temperature of from 1° C. to 10° C. for at least about 30 days, at least about 60 days or at least about 90 days from packaging. It is particularly preferred that the lactic acid bacteria is selected from the group consisting of CNCM I-1631 & CNCM I-3862.

According to a further embodiment, the composition further comprises an intermediate preparation comprising a preparation of fruits and/or cereals and/or additives such as flavorings and/or colorings. Said intermediate preparation can in particular contain thickeners (soluble and insoluble fibres, alginates, carragheenans, xanthan gum, pectin, starch, in particular gelatinized, gelan gum, cellulose and its derivatives, guar and carob gum, inulin) or sweeteners (aspartame, acesulphame K, saccharine, sucralose, cyclamate) or preservatives. Examples of flavorings are: apple, orange, strawberry, kiwi fruit, cocoa flavoring etc. Examples of colorings are: beta-carotene, carmine, cochineal red. Moreover, the preparation of the abovementioned fruits can comprise fruits which are whole or in pieces or in jelly or in jam, making it possible for example to obtain fruit yogurts.

Preferably the composition according to embodiments of the invention comprises up to about 30% (w/w) of said intermediate preparation, e.g. up to about 10%, 15%, 20%, 25% (w/w). In one embodiment, the composition according to embodiments of the invention comprise 1% to 30% (w/w) of said intermediate preparation. In alternative embodiments, the composition according to embodiments of the invention comprise 1% to 25% (w/w) of said intermediate preparation. In further alternative embodiments, the composition according to embodiments of the invention comprise 1% to 20% (w/w) of said intermediate preparation. In additional embodiments, the composition according to embodiments of the invention comprise 1% to 15% (w/w) of said intermediate preparation. In further additional embodiments, the composition according to embodiments of the invention comprise 1% to 10% (w/w) of said intermediate preparation.

Preferably the composition, according to embodiments of the invention is provided in a sealed or sealable container containing about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g, 320 g or 500 g or about 1 oz, 2 oz, 3 oz, 4 oz, 5 oz, 6 oz or 12 oz product by weight.

In embodiments, the composition, according to embodiments of the invention is provided in a sealed or sealable container containing about 50 g to 500 g, 60 g to 500 g, 70 g to 500 g, 75 g to 500 g, 80 g to 500 g, 85 g to 500 g, 90 g to 500 g, 95 g to 500 g, 100 g to 500 g, 105 g to 500 g, 110 g to 500 g, 115 g to 500 g, 120 g to 500 g, 125 g to 500 g, 130 g to 500 g, 135 g to 500 g, 140 g to 500 g, 145 g to 500 g, 150 g to 500 g, 200 g to 500 g, 300 g to 500 g, 320 g to 500 g or 500 g product by weight. In embodiments, the composition, according to embodiments of the invention is provided in a sealed or sealable container containing about 1 oz to 12 oz, 2 oz to 12 oz, 3 oz to 12 oz, 4 oz to 12 oz, 5 oz to 12 oz, 6 oz to 12 oz or 12 oz product by weight.

Methods for the Preparation of Fermented Milk Products

Methods for the preparation of fermented milk products, such as yogurts or equivalents thereof, are well-known in the art.

Preferably fermented milk products are prepared using milk that has been subjected to heat treatment at least equivalent to pasteurization. Preferably said heat treatment is carried out prior to the preparation of the composition.

Typically, milk is pasteurized by means of the following successive steps:

1) standardization of fatty substances of the raw material so as to obtain a standardized substance,
2) enrichment with dried matter of the standardized substance obtained in the preceding stage, so as to obtain an enriched substance,
3) preheating of the enriched substance obtained in the preceding stage, so as to obtain a starting substance,
4) pasteurization and holding of the starting substance obtained in the preceding stage, so as to obtain a pasteurized and held substance,
5) an optional stage of homogenization of the pasteurized and held substance obtained in the preceding stage, so as to obtain a pasteurized, held and optionally homogenized substance,
6) initial cooling of the pasteurized, held and optionally homogenized substance obtained in the preceding stage, so as to obtain a pasteurized starting substance that has been held, optionally homogenized, and cooled down.

As used herein "standardization of fatty substances" is taken to mean a stage of bringing the quantity of fats present in the starting substance to a pre-determined level. Enrichment with dried matter involves the addition of proteins and fatty substance in order to modify curd firmness.

As used herein "holding" is taken to mean a rapid thermalization of the milk and makes it possible to destroy the vegetative microbial flora, including pathogenic forms. Its typical duration is from 4 to 10 minutes, in particular from 5 to 8 minutes, and in particular approximately 6 minutes.

As used herein "homogenization" is taken to mean the dispersion of the fatty substances in the milk-type substance into small fat globules. The homogenization is carried out for example at a pressure of 100 to 280 bars, in particular 100 to 250 bars, in particular 100 to 200 bars, in particular approximately 200 bars. This homogenization stage is purely optional. It is in particular absent from the production process of products with 0% fatty substances.

Typically a fermented milk product is prepared by culture of milks at a suitable temperature with suitable microorganisms to provide a reduction in pH, preferably to a pH equal to or lower than 5, preferably between about 3 and 4.5; more preferably between about 3.5 and about 4.5. The pH can be adjusted by controlling the fermentation by the microorganism and stopping it when appropriate, for example by cooling.

The selection of suitable lactic acid bacteria strains is within the scope of the skilled person and is typically a thermophillic lactic acid bacteria. Examples of lactic acid bacteria that can be used include but are not limited to Lactobacilli (for example *Lactobacillus acidophilus, Lacto-* bacillus buchneri, Lactobacillus delbruckei, in particular *L. delbruckei* supsb. *bulgaricus* or *lactis*, *Lactobacillus casei*, *Lactobacillus plantarum*, *Lactobacillus reuteri*, *Lactobacillus johnsonii*, *Lactobacillus helveticus*, *Lactobacillus brevis*, *Lactobacillus rhamnosus*); Streptococci (for example *Streptococcus thermophilus*); Lactococci (for example *Lactococcus lactis*, typically *Lactococcus lactis* subsp. *lactis* or *Lactococcus lactis* subsp. *cremoris*). Typically a mixture or association of a plurality of species of lactic acid bacteria may be used, typically a mixture or association of *Lactobacillus* and *Streptococcus*. For the preparation of yogurt this typically includes *Lactobacillus bulgaricus* (also referred to as *Lactobacillus delbruckei* subsp. *bulgaricus*) and *Streptococcus thermophilus*, optionally with additional microorganisms such as but not limited to probiotic species or other species that may provide desirable organoleptic or other qualities to the composition, e.g. *Lactococcus lactis*. It is particularly preferred that the lactic acid bacteria are selected from the group consisting of CNCM I-1631 & CNCM I-3862.

Suitable temperatures for milk fermentation are typically about 36° C. to about 44° C. and the temperature is maintained for an incubation time sufficient to provide the desired reduction in pH.

For the preparation of a fermented milk product the temperature at the start of fermentation is typically about 36° C. to about 43° C., in particular about 37° C. to about 40° C., the temperature at the end of fermentation is typically about 37° C. to about 44° C., in particular about 38° C. to about 41° C. The fermentation time is typically about 6 to about 11 hours.

Subsequent to the fermentation the fermented milk is cooled. Optionally a stage of intermediate cooling of the fermented milk may be performed to provide a pre-cooled fermented milk having a temperature of between about 22° C. and about 4° C. Typically the intermediate cooling time is about 1 hour to about 4 hours, in particular about 1 hour 30 minutes to about 2 hours. The pre-cooled fermented milk is typically stored for up to 40 hours or less.

Preferably a stage of final cooling of the fermented milk is performed such that the temperature at the start of the final cooling is less than about 22° C. and the temperature at the end of the final cooling is about 4° C. to about 10° C. The cooled product may then be stored, transported and/or distributed at a temperature from about 1° C. to about 10° C. for at least about 30 days, at least about 60 days or at least about 90 days.

According to a further embodiment, the process for the preparation of a fermented milk product as defined above optionally comprises a stage of stirring at a pressure of at least 20 bars, or performing a dynamic smoothing, to obtain a composition having the desired viscosity, typically a viscosity of up to 20 mPa·s. Stirring or dynamic smoothing operations provide some shear to composition that typically allow a viscosity drop. Such operations are known by the one skilled in the art, and can be operated with conventional appropriate equipment. This stage is typically performed at cold temperature, for example at a temperature of form 1° C. to 20° C. Without intending to be bound to any theory, it is believed that applying some shear at cold temperature, typically by stirring at high pressure or by performing a dynamic smoothing, can lead to a fluid gel formation within the composition, that provides improved stability even at a low viscosity of up to 20 mPa·s.

According to a further embodiment, the process for the preparation of a fermented milk product as defined above optionally comprises a stage of addition of an intermediate preparation prior or subsequent to fermentation, said intermediate preparation comprising a preparation of fruits and/or cereals and/or additives such as flavorings and/or colorings.

In one aspect the the present invention also provides a *Streptococcus thermophilus* strain deposited at the CNCM under reference number I-3862. The present invention also provides a fermented milk product comprising a *Streptococcus thermophilus* strain deposited at the CNCM under reference number I-3862.

The invention will be further illustrated by the following non-limiting Figures and Example.

EXAMPLE

Material and Methods

Bacterial Strains, Media and Supernatants Production

Figure 1:
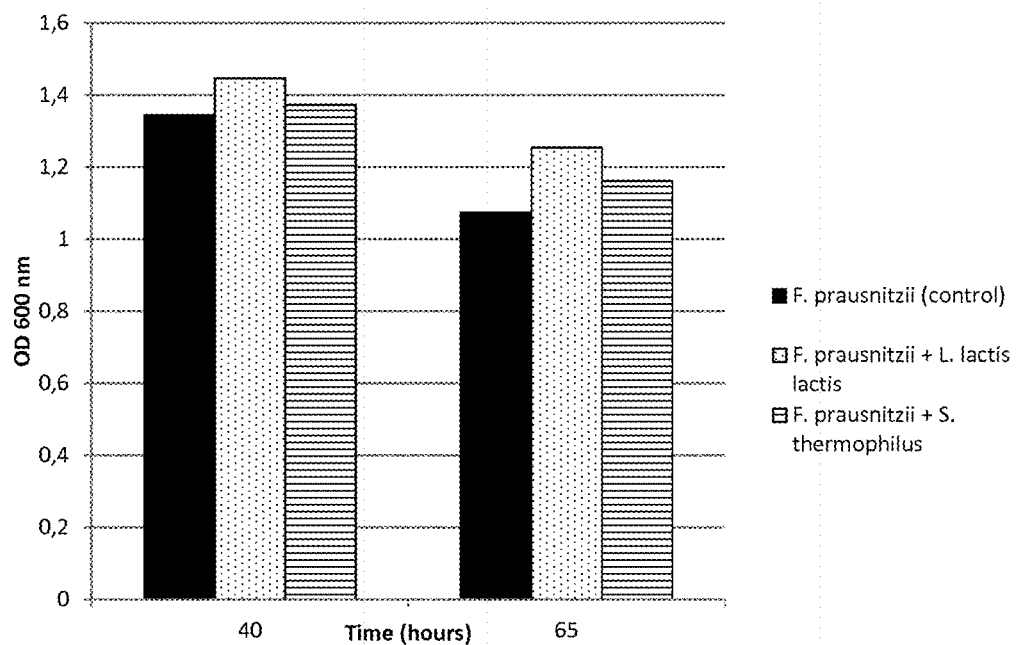
FIG. 1 represents the optical density (OD) at 600 nm (vertical axis) of a culture of *Faecalibacterium prausnitzii* without (black bar, control) or with the addition of a culture supernatant from *Lactococcus lactis* subsp. *lactis* (dotted bar) or from *Streptococcus thermophilus* (hatched bar), after a culture time of 40 hours and 65 hours (horizontal axis).

The bacterial strains used in this study are listed in Table 1. Purity of all strains was regularly assessed by microscopy observation after cell staining. *Faecalibacterium prausnitzii* was purchased from the Deutsche Sammlung von Mikroorganismen und Zellkulturen (DSMZ) (DSM 17677). They were all grown in Brain-heart infusion medium (Becton Dickinson) supplemented with 0.5% yeast extract (Becton Dickinson) and 5 mg/L hemin chloride (Calbiochem), supplemented with cellobiose (1 g/L; Sigma-Aldrich), maltose (1 g/L; Sigma-Aldrich), and cysteine (0.5 g/L; Sigma-Aldrich) in an anaerobic chamber, with the following gas mixture, 80% $N_2$— 10% $CO_2$— 10% $H_2$. When the culture was grown, glycerol solution was added (16 g/L; Sigma-Aldrich). 2 mL aliquots stock were prepared and kept at −20° C. For each experiment, a new aliquot was used. For probiotics—*Faecalibacterium prausnitzii* interaction tests, all strains were grown in YCFA medium (pH 6) that was optimized in order to allow growth of all bacterial strains (Table 2). This medium consisted of glucose (20 g/L, Sigma-Aldrich), tryptone (10 g/L, Becton Dickinson), yeast extract (5 g/L, Becton Dickinson), sodium acetate (5 g/L, Sigma-Aldrich), monohydrate lactose (5 g/L, Sigma-Aldrich), sodium bicarbonate (4 g/L, Sigma-Aldrich), cellobiose (2 g/L, Sigma-Aldrich), sodium chloride (0.9 g/L, Sigma-Aldrich), ammonium sulfate (0.9 g/L, Sigma-Aldrich), cysteine (0.5 g/L, Sigma-Aldrich), dibasic potassium phosphate (0.45 g/L, Sigma-Aldrich), magnesium sulfate (0.09 g/L, Sigma-Aldrich), calcium chloride (0.09 g/L, Sigma-Aldrich), hemin chloride (0.01 g/L Sigma-Aldrich), resazurine sodium salt (0.001 g/L, Alfa Aesar). This medium was reduced in anaerobic chamber and autoclaved before use.

TABLE 1

List of strains used in this study

| Name | Usual medium |
| --- | --- |
| Lactobacillus lactis subsp lactis CNCM I-1631 | M17 with lactose |
| Streptococcus thermophilus CNCM I-3862 | M17 with lactose |
| F. prausnitzii DSM 17 677 | BHI |

TABLE 2

Composition of YCFA optimized for this study

| Component | g/L (1 L) |
| --- | --- |
| Yeast Extract | 5 |
| Celllobiose | 2 |
| Tryptone | 10 |
| Dibasic Potassium phosphate | 0.45 (450 mg) |
| Sodium chloride | 0.9 (900 mg) |
| Ammonium sulfate | 0.9 (900 mg) |
| Magnesium sulfate | 0.09 (90 mg) |
| Calcium chloride | 0.09 (90 mg) |
| Resazurine sodium salt 0.01% | 10 mL |
| Sodium bicarbonate 4% | 100 mL |
| Sodium acetate 5% | 100 mL |
| Hemin chloride 1% + 0.4 mL NaOH 5M | 1 mL |
| Monohydrate lactose 5% | 100 mL |
| Glucose10% | 200 mL |
| Cysteine 5% | 10 mL |

Bacterial Supernatants Preparation

Bacterial supernatants were produced as follows: Strains were grown in 2 mL of usual growth media and atmosphere (Table 1) at 37° C. After 24 h-growth, the cells were inoculated at 1% in 10 mL of usual growth media and atmosphere (Table 1) at 37° C. Lastly, these cultures were inoculated at 1% in 50 mL of YCFA, previously reduced as described above, at 37° C. for 24 h. Cultures were pelleted at 7500 g for 10 min, supernatants were filtered at 0.2 µm and directly frozen at −20 degrees.

Tests of Stimulation of *Faecalibacterium prausnitzii* DSM 17677 by Lactic Acid Bacteria Before use, the bacterial supernatants were allowed to reduce in the anaerobic chamber for 2 hours. Then, 4 ml of reduced supernatants from the bacterial strains were added to 50 mL of YCFA. As a control, 4 ml of sterile YCFA were added to 50 ml of YCFA. Subsequently, a 48 hours culture of *F. praunistzii* was inoculated at 1% into the YCFA medium. Growth was monitored over 72 hours. OD and pH were measured at regular interval during the growth (hours). Samples were collected and stored for DNA extraction (see below). Additional samples were collected for further analysis (DNA, SCFA analysis, metabolomics and transcriptomics).

Metabolites Analysis 2 mL of fresh culture were collected and centrifuged at 10 000 g for 15 minutes. Supernatants were filtered (0.2 µm) and stored at −20° C. until analysis.

Samples for short-chain fatty acid (SCFA) and branched chain fatty acids (BCFA) analysis were collected after 16, 22 and 40 h. They were measured quantitatively. Short-chain fatty acid (SCFA) Acetate, propionate, butyrate, valerate, caproate and branched chain fatty acids (BCFA) isobutyrate, isovalerate and isocaproate as well as lactate were measured at Prodigest as follow: SCFA were extracted from the samples with diethyl ether, after the addition of 2-methyl hexanoic acid as an internal standard. Extracts were analysed using a GC-2014 gas chromatograph (Shimadzu, 'S-Hertogenbosch, the Netherlands), equipped with a capillary fatty acid-free EC-1000 Econo-Cap column (dimensions: 25 mm 0.53 mm, film thickness 1.2 mM; Alltech, Laarne, Belgium), a flame ionization detector and a split injector. The injection volume was 1 mL and the temperature profile was set from 110 to 160° C., with a temperature increase of 6° C./min. The carrier gas was nitrogen and the temperature of the injector and detector were 100 and 220° C., respectively. The production of unbranched and branched SCFA was calculated by summing the molar concentrations of acetate, propionate, butyrate, valerate and caproate, and summing isobutyrate, isovalerate and isocaproate molar concentrations, respectively. The total SCFA production was defined as the sum of unbranched and branched SCFA. Lactate was measured using a D-lactate/L-lactate kit (R-Biopharm, Mannheim, Germany), according to the manufacturer's protocols.

Results

The results of the stimulation of *F. prausnitzii* growth by the culture supernatants of *S. thermophilus* and *Lactococcus lactis* subsp. *lactis* are shown in FIG. 1. It can be seen that both supernatants yield an increase of the growth of *F. prausnitzii* after 40 hours and 65 hours of culture.

Figure 2:
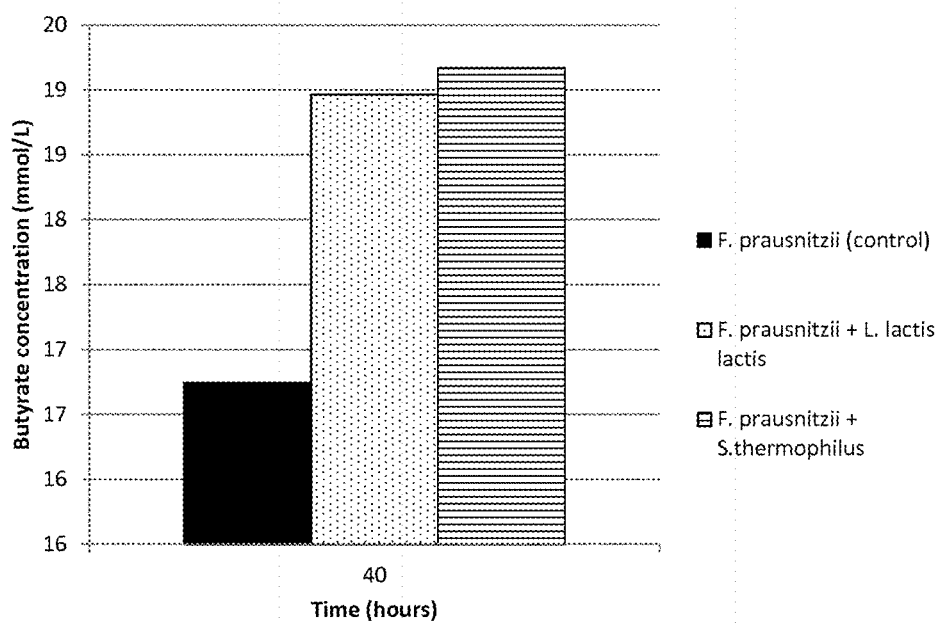
FIG. 2 represents the concentration of butyrate (in mmol/L, vertical axis) of a culture of *Faecalibacterium prausnitzii* without (black bar, control) or with the addition of a culture supernatant from *Lactococcus lactis* subsp. *lactis* (dotted bar) or from *Streptococcus thermophilus* (hatched bar), after a culture time of 40 hours (horizontal axis).

The results of the stimulation of butyrate production by *F. prausnitzii* growth by the culture supernatants of *S. thermophilus* and *Lactococcus lactis* subsp. *lactis* are shown in FIG. 2. After 40 hours of incubation, there was a 15% increase of butyrate production in presence of *S. thermophilus* and *L. lactis lactis* supernatant compared to the single culture (19.2 mmol/L±3.6 mmol/L, 19.0 mmol/L±0.8 mmol/L and 16.7 mmol/L±1 mmol/L respectively).

The invention claimed is:

1. A fermented food product comprising milk and a *Streptococcus thermophilus* strain deposited at the CNCM under reference number I-3862, wherein the milk is heat treated prior to preparing the fermented food product.

2. The fermented food product of claim 1, wherein the food product is a dairy product.

3. The fermented food product of claim 2, wherein the dairy product is yogurt, set yogurt, stirred yogurt, pourable yogurt, a yogurt drink, frozen yogurt, kefir, buttermilk, quark, sour cream, or cheese.

4. The fermented food product of claim 1, wherein the food product is a drinkable composition.

5. The fermented food product of claim 4, wherein the food product is a yogurt drink or kefir.

6. The fermented food product of claim 1, wherein the food product is spoonable.

7. The fermented food product of claim 6, wherein the food product is set or stirred yogurt.

8. The fermented food product of claim 1, wherein the milk is animal milk.

9. The fermented food product of claim 1, wherein the milk is vegetal milk.

10. The fermented food product of claim 1, wherein the milk is pasteurized prior to preparing the fermented food product.

11. A method of preparing a fermented food product of claim 1, comprising culturing heat treated milk and a *Streptococcus thermophilus* strain deposited at the CNCM under reference number I-3862.

12. The method of claim 11, wherein the culturing is performed from about 36° C. to about 44° C.

13. The method of claim 12, wherein the culturing is performed from about 37° C. to about 40° C.

14. The method of claim 11, wherein the culturing reduces the pH of the product to a pH of equal to or lower than 5.

15. The method of claim 14, wherein the culturing reduces the pH of the product to between about 3 and 4.5.

16. The method of claim 11, wherein the food product is a dairy product.

17. The method of claim 16, further comprising culturing *Lactobacillus delbruckei* subsp. *bulgaricus*.

* * * * *